US008636811B2

(12) United States Patent
Melder

(10) Patent No.: US 8,636,811 B2
(45) Date of Patent: Jan. 28, 2014

(54) DRUG ELUTING ROLLED STENT AND STENT DELIVERY SYSTEM

(75) Inventor: Robert J. Melder, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 733 days.

(21) Appl. No.: 12/755,585

(22) Filed: Apr. 7, 2010

(65) Prior Publication Data
US 2011/0251663 A1 Oct. 13, 2011

(51) Int. Cl.
*A61F 2/02* (2006.01)

(52) U.S. Cl.
USPC ..... 623/23.72; 623/1.11; 623/1.42; 623/1.44; 623/1.46

(58) Field of Classification Search
USPC .......... 623/1.11, 1.42–1.44, 1.46, 1.13, 23.72
See application file for complete search history.

(56) References Cited

U.S. PATENT DOCUMENTS

| 5,605,696 | A | | 2/1997 | Eury et al. | |
|---|---|---|---|---|---|
| 5,637,113 | A | * | 6/1997 | Tartaglia et al. | 623/1.42 |
| 5,718,973 | A | * | 2/1998 | Lewis et al. | 623/1.32 |
| 5,735,892 | A | * | 4/1998 | Myers et al. | 623/1.13 |
| 5,766,710 | A | * | 6/1998 | Turnlund et al. | 623/1.15 |
| 5,824,054 | A | | 10/1998 | Khosravi et al. | |
| 5,984,963 | A | * | 11/1999 | Ryan et al. | 623/1.11 |
| 6,264,687 | B1 | | 7/2001 | Tomonto | |
| 6,290,721 | B1 | | 9/2001 | Heath | |
| 6,290,722 | B1 | * | 9/2001 | Wang | 623/1.46 |
| 6,425,855 | B2 | | 7/2002 | Tomonto | |
| 6,824,559 | B2 | * | 11/2004 | Michal | 623/1.15 |
| 6,849,085 | B2 | | 2/2005 | Marton | |
| 7,765,670 | B2 | * | 8/2010 | Spencer et al. | 29/451 |
| 7,901,447 | B2 | * | 3/2011 | Molaei et al. | 623/1.15 |
| 8,206,433 | B2 | * | 6/2012 | Rucker | 623/1.21 |
| 8,348,989 | B2 | * | 1/2013 | Chobotov et al. | 623/1.13 |
| 8,425,586 | B2 | * | 4/2013 | Leopold et al. | 623/1.15 |
| 2003/0093140 | A1 | * | 5/2003 | Wall | 623/1.11 |
| 2004/0215336 | A1 | * | 10/2004 | Udipi et al. | 623/1.42 |
| 2005/0163821 | A1 | * | 7/2005 | Sung et al. | 424/426 |
| 2006/0224235 | A1 | * | 10/2006 | Rucker | 623/1.21 |
| 2007/0250158 | A1 | | 10/2007 | Krivoruchko et al. | |
| 2008/0208313 | A1 | | 8/2008 | Yu et al. | |
| 2009/0326639 | A1 | * | 12/2009 | Edin | 623/1.15 |
| 2010/0106255 | A1 | * | 4/2010 | Dubin | 623/23.7 |
| 2010/0122698 | A1 | * | 5/2010 | Shaffer et al. | 128/204.18 |

(Continued)

FOREIGN PATENT DOCUMENTS

| WO | WO 94/21196 | 9/1994 |
|---|---|---|
| WO | WO 2006/093880 | 9/2006 |
| WO | WO 2010/047929 | 4/2010 |

*Primary Examiner* — Thomas J Sweet
*Assistant Examiner* — Seema Mathew

(57) ABSTRACT

The drug eluting rolled stent and a stent delivery system, which includes a catheter; a balloon operably attached to the catheter; and a stent disposed on the balloon. The stent includes a rectangular metal foil sheet having a first side and a second side, the rectangular metal foil sheet being rolled to form a cylindrical tube having a central axis and a spiral cross section perpendicular to the central axis; a polymer drug coating disposed between and adhering the first side and the second side; and at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

14 Claims, 8 Drawing Sheets

(56) References Cited

U.S. PATENT DOCUMENTS

2011/0054588 A1* 3/2011 Xu et al. ............... 623/1.13
2012/0277843 A1* 11/2012 Weber et al. ........... 623/1.11
2013/0204343 A1* 8/2013 Shalev ................... 623/1.11

* cited by examiner

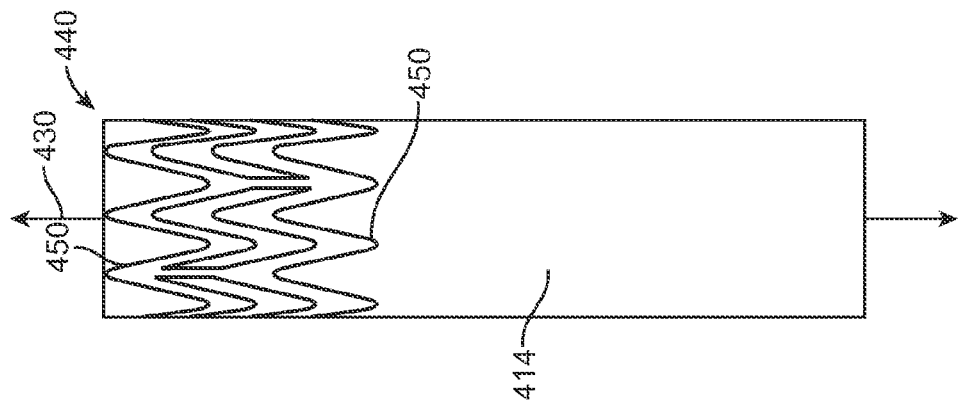
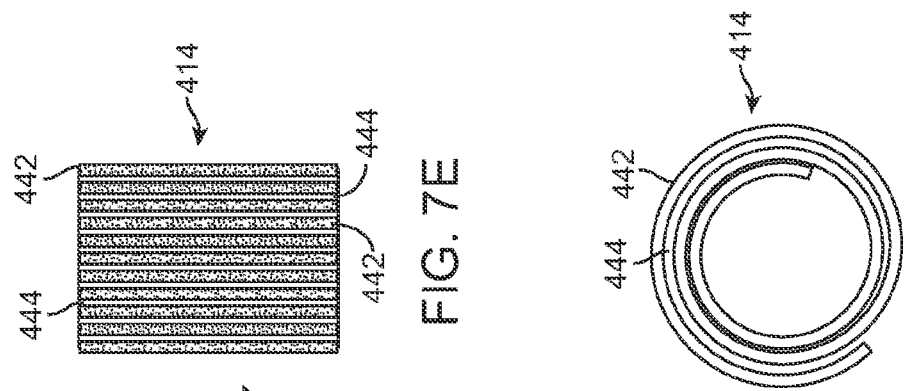
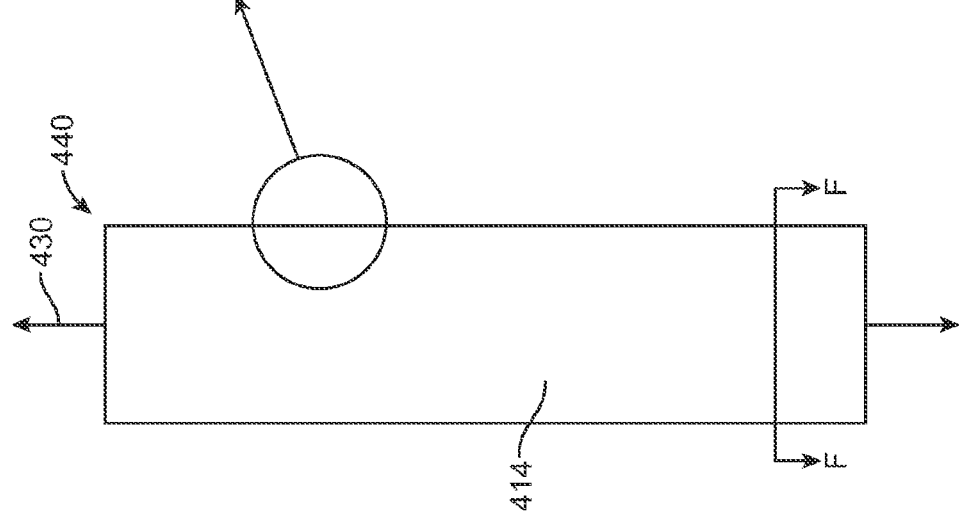

DRUG ELUTING ROLLED STENT AND STENT DELIVERY SYSTEM

TECHNICAL FIELD

The technical field of this disclosure is medical implant devices, particularly, drug eluting rolled stents and stent delivery systems.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Drug eluting stents currently employ exterior coatings with or without polymers on metal struts to hold a drug for subsequent elution and delivery of the drug to surrounding tissue. Unfortunately, such coatings present a number of problems and limitations. The coatings are fragile and can fracture and fragment during manufacture, delivery, deployment, or use. Fracture during manufacture increases the cost and complexity of manufacture. Fracture during delivery, deployment, or use can reduce the effectiveness of the stent due to lost drug and can pose a risk to the patient if fragments block blood flow. The drug elutes from the coating surface, so the duration of drug elution is limited by the coating thickness, i.e., the mean diffusion length of the drug within the polymer coating. In addition, metal struts can fatigue and cracks can propagate through metal struts during use, fracturing the metal struts and creating fragments which can present a hazard to the patient. Concerns have also been raised over the long-term effects of polymers in contact with the body.

It would be desirable to have a drug eluting rolled stent and stent delivery system that would overcome the above disadvantages.

SUMMARY OF THE INVENTION

One aspect of the present invention provides a stent delivery system including a catheter; a balloon operably attached to the catheter; and a stent disposed on the balloon. The stent includes a rectangular metal foil sheet having a first side and a second side, the rectangular metal foil sheet being rolled with the first side across from the second side to form a cylindrical tube having a central axis and a spiral cross section perpendicular to the central axis; a polymer drug coating disposed between and adhering the first side and the second side; and at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

Another aspect of the present invention provides a stent including a rectangular metal foil sheet having a first side and a second side, the rectangular metal foil sheet being rolled with the first side across from the second side to form a cylindrical tube having a central axis and a spiral cross section perpendicular to the central axis; a polymer drug coating disposed between and adhering the first side and the second side; and at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

Another aspect of the present invention provides a method of manufacturing a stent including providing a rectangular metal foil sheet having a first side and a second side; applying a polymer drug coating to the first side of the rectangular metal foil sheet to form a coated sheet; maintaining the polymer drug coating in an adhesive state; rolling the coated sheet around a mandrel to form a cylindrical tube having a central axis and a spiral cross section perpendicular to the central axis, the polymer drug coating bridging between the first side and the second side of the coated sheet; solidifying the polymer drug coating to adhere the first side and the second side of the coated sheet; and forming at least one opening through the cylindrical tube generally perpendicular to the central axis, the at least one opening being shaped to form at least one strut having in cross section polymer drug layers between metal foil layers.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 7A-7G are various views of a method of manufacture of a drug eluting rolled stent in accordance with the present invention.

DETAILED DESCRIPTION

Figure 1:
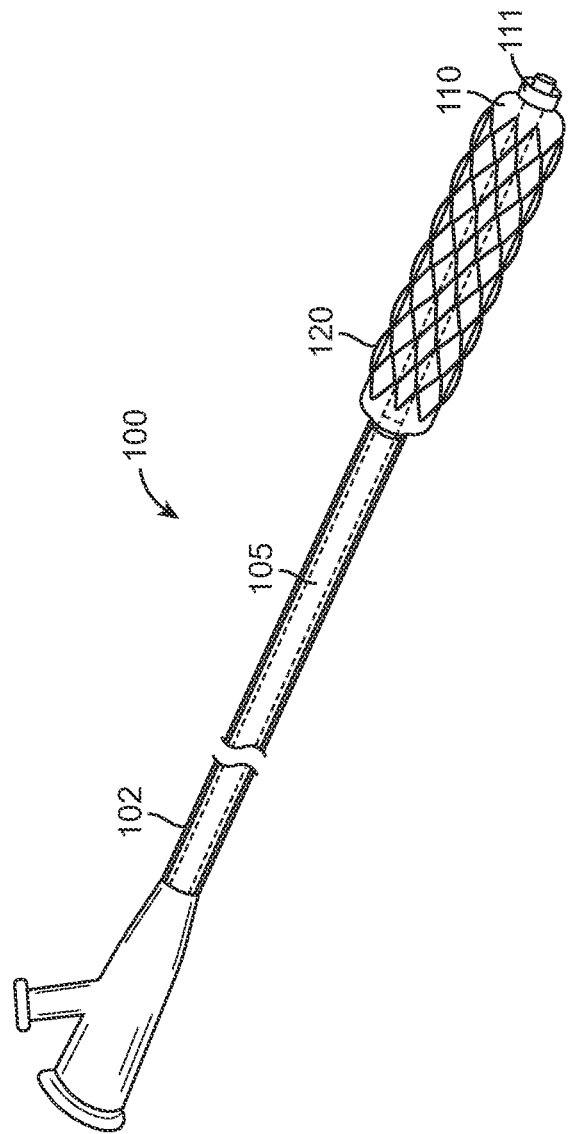
FIG. 1 is a perspective view of a stent delivery system made in accordance with the present invention.

FIG. 1 is a perspective view of a stent delivery system made in accordance with the present invention. The stent delivery system 100 includes a catheter 105, a balloon 110 operably attached to the catheter 105, and a stent 120 disposed on the balloon 110. The stent 120 is operable for use in a vessel having a vessel wall forming a vessel lumen. The stent 120 includes at least one strut operable to support the vessel wall when the stent 120 is in an expanded condition.

The balloon 110, shown in an inflated state, can be any variety of balloons capable of expanding the stent 120. The balloon 110 can be manufactured from a material such as polyethylene, polyethylene terephthalate (PET), nylon, Pebax® polyether-block co-polyamide polymers, or the like. In one embodiment, the stent delivery system 100 can include retention means 111, such as mechanical or adhesive structures, for retaining the stent 120 on the balloon 110 until the stent 120 is deployed. The catheter 105 may be any variety of balloon catheter, such as a PTCA (percutaneous transluminal coronary angioplasty) balloon catheter, capable of supporting a balloon during angioplasty. The stent delivery system 100 can also include a sheath 102 through which the stent 120 can be delivered to the deployment site.

Figure 2:
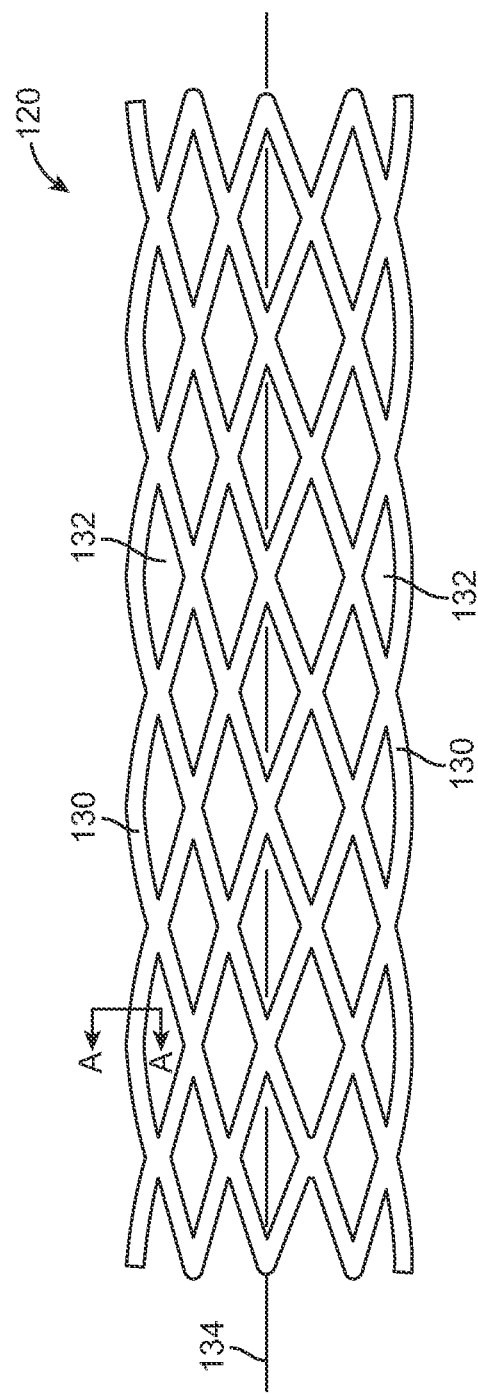
FIG. 2 is a side view of a drug eluting rolled stent made in accordance with the present invention.

FIG. 2 is a side view of a drug eluting rolled stent made in accordance with the present invention. The stent 120 can be installed in the stent delivery system of FIG. 1 for implantation in a body lumen, such as a vessel lumen. The stent includes a rectangular metal foil sheet having a first side and a second side, the rectangular metal foil sheet being rolled with the first side across from the second side to form a cylindrical tube having a central axis and a spiral cross section perpendicular to the central axis; a polymer drug coating disposed between and adhering the first side and the second side; and at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

Referring to FIG. 2, the stent 120 includes at least one opening 132 and at least one strut 130. The stent 120 includes a rectangular metal foil sheet rolled into a cylindrical tube with a spiral cross section and has a central axis 134 with openings 132 formed generally perpendicular to the central axis. A polymer drug coating is disposed between opposite sides of the rectangular metal foil sheet. In this example, the stent 120 is a web stent, which is defined herein as a stent in which the pattern of the openings 132 is shaped to form a web of the struts 130. The pattern of the struts 130 can be W-shaped or can be a more complex shape with the elements of one segment continuing into the adjacent segment. In another embodiment, the stent 120 can be a helical stent (not shown), which is defined herein as a stent in which the opening is a single continuous helix shaped to form a single continuous helix of a single strut. In one embodiment, the stent 120 can be expanded by a balloon or some other device. In another embodiment, the stent 120 can be self-expanding.

Figure 3:
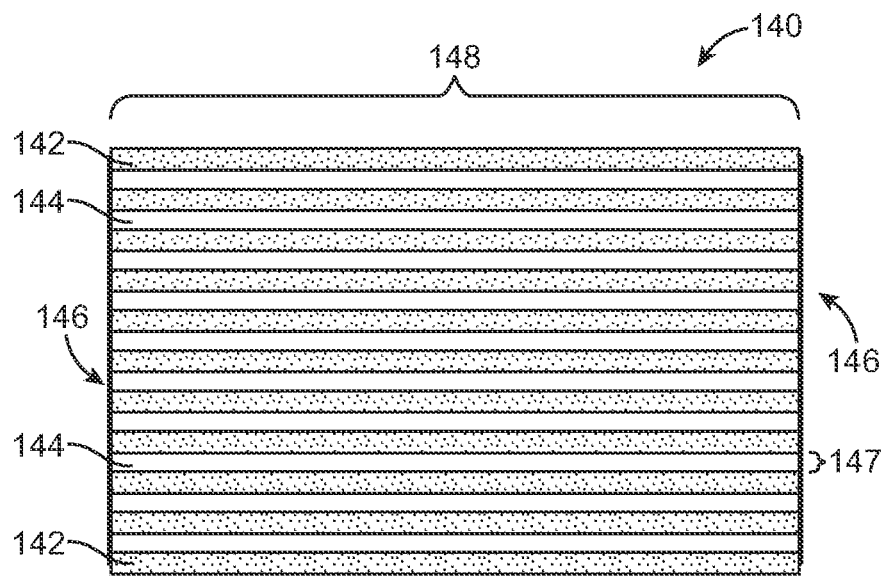
FIG. 3 is a cross section view of a strut of a drug eluting rolled stent made in accordance with the present invention.

FIG. 3 is a cross section view of a strut of a drug eluting rolled stent made in accordance with the present invention. The strut has a cross section of polymer drug layers, which are part of the polymer drug coating, between metal foil layers, which are part of the rectangular metal foil sheet. The polymer drug layers are attached to the metal foil layers to form a unitary structure. The cross section view is taken at Section A-A of FIG. 2.

Referring to FIG. 3, the strut 140 includes a number of polymer drug layers 144 between metal foil layers 142. The polymer drug layers 144 elute one or more drugs from the polymer drug layer edges 146 of the polymer drug layers 144 into the openings in the stent, into the vessel lumen and/or vessel wall. The polymer drug layer edges 146 are in communication with the openings. The polymer drug layers 144 can all contain the same drug or can contain different drugs, i.e., a first radial polymer drug layer can include one drug and a second radial polymer drug layer can include another drug different from the drug in the first radial polymer drug layer. Different drugs in different radial polymer drug layers allow one drug to be delivered near the vessel wall and another drug to be delivered into the vessel lumen.

The dimensions of the strut 140 can be selected to provide desired mechanical characteristics, a predetermined drug elution rate, and a predetermined drug elution duration. The materials and thickness of the polymer drug layers 144 and metal foil layers 142 can be selected to provide the desired stiffness and resiliency. In one embodiment, each of the polymer drug layers 144 has a thickness 147 selected to provide a predetermined drug elution rate. The thicker the polymer drug layer, the greater the drug reservoir and surface area available for drug release, and consequently, the more quickly and longer the drug can be eluted from the polymer drug layer. In another embodiment, the strut 140 has a width 148 selected to provide a predetermined drug elution duration. The greater the width of the strut 140, the greater the available drug reservoir and the further the drug diffuses through the polymer drug layer before exiting the polymer drug layer edges 146, extending the drug elution duration. In one example, the strut 140 has a width of 90 μm and a thickness of 90 μm, assembled from four polymer drug layers each having a thickness of 10 μm and five metal foil layers each having a thickness of 10 μm. In another example extending elution duration, the strut 140 has a width of 180 μm and a thickness of 90 μm. In yet another example increasing radial strength and decreasing the rate and amount of delivered drug, the strut 140 has a width of 90 μm and a thickness of 85 μm, assembled from two polymer drug layers each having a thickness of 10 μm and three metal foil layers each having a thickness of 25 μm.

Figure 4:
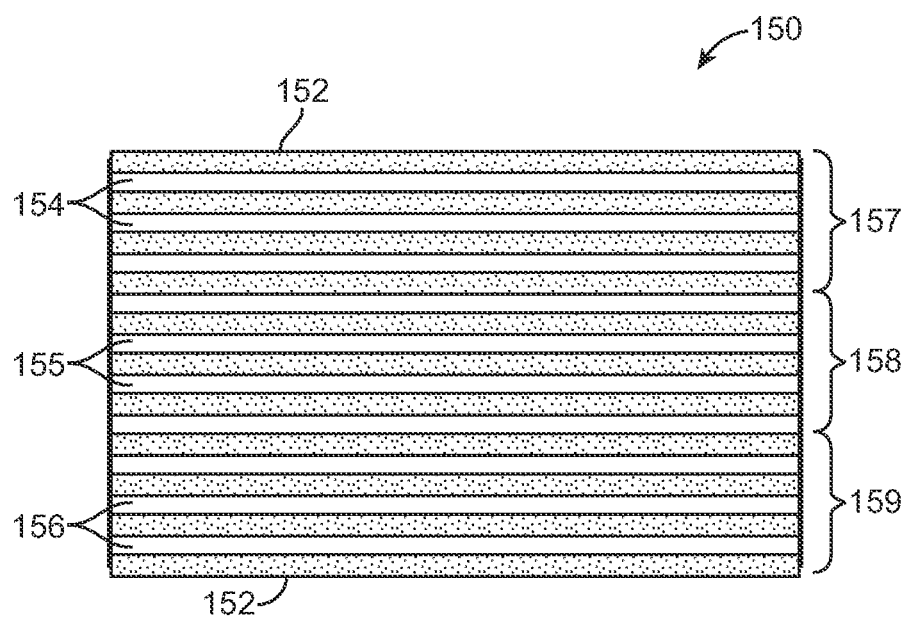
FIG. 4 is a cross section view of another embodiment of a strut of a drug eluting rolled stent made in accordance with the present invention.

FIG. 4 is a cross section view of another embodiment of a strut of a drug eluting rolled stent made in accordance with the present invention. In this embodiment, the polymer drug layers are grouped into radial zones having the same drug or drugs in a single radial zone. The strut 150 includes a number of polymer drug layers 154, 155, 156 between metal foil layers 152. Each of the polymer drug layers 154, 155, 156 elute one or more drugs from the polymer drug layer edges of the polymer drug layers into the openings in the stent, into the vessel lumen and/or vessel wall. The polymer drug layer edges are in communication with the openings. The polymer drug layers 154, 155, 156 are grouped into radial zones 157, 158, 159, with each of the polymer drug layers in a single radial zone having the same drug or drugs. Different drugs in different radial zones 157, 158, 159 allow one drug to be delivered near the vessel wall and another drug to be delivered into the vessel lumen. In one embodiment, the polymer drug layers in at least one of the radial zones include polymer alone without drug.

Figure 5:
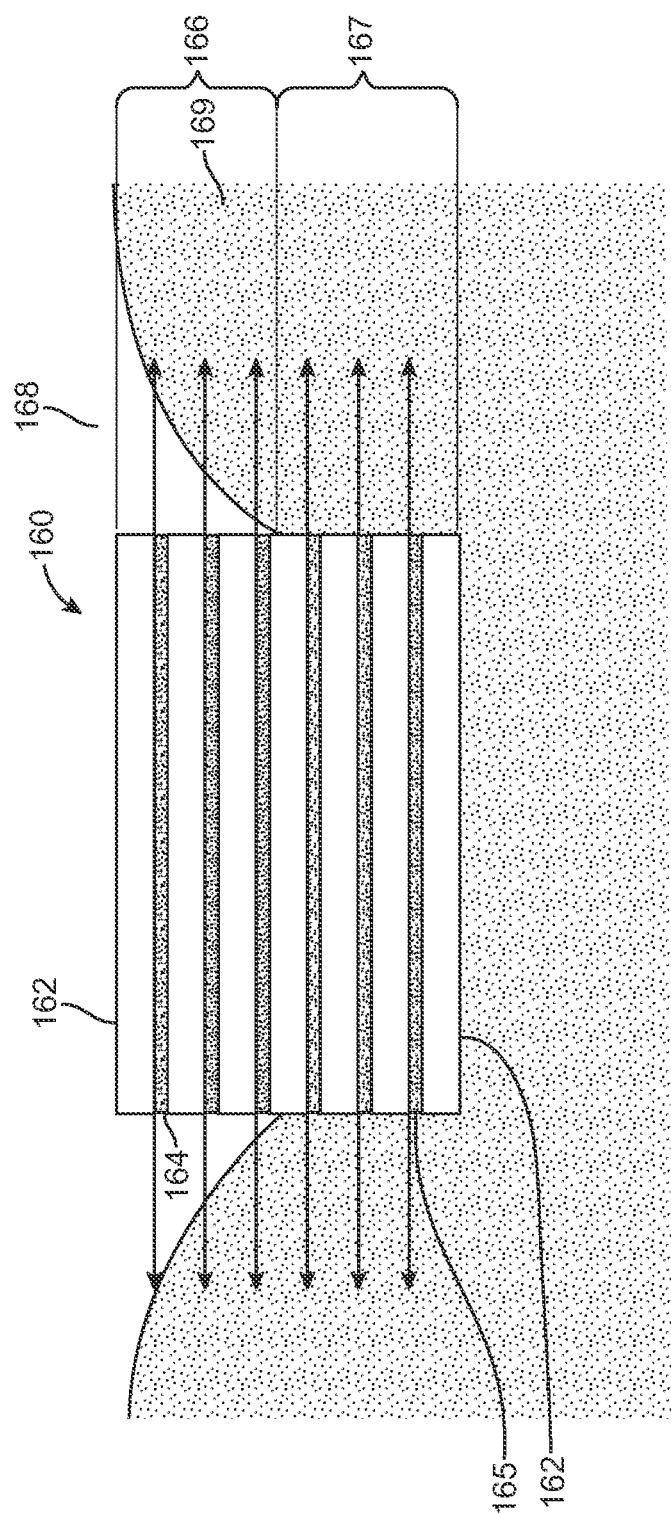
FIG. 5 is a cross section view of a strut of a deployed drug eluting rolled stent made in accordance with the present invention in an expanded condition.

FIG. 5 is a cross section view of a strut of a deployed drug eluting rolled stent made in accordance with the present invention in an expanded condition, i.e., when deployed in a vessel. In this example, the strut includes polymer drug layers grouped into two radial zones, with each radial zone eluting a different drug as indicated by the arrow. Such a configuration facilitates simultaneous delivery of two or more drugs without co-formulating the drugs in the same matrix, facilitating the use of drugs and drug-polymer matrices in adjacent layers with non-compatible chemistries. The strut 160 includes a number of polymer drug layers 164, 165 between metal foil layers 162 in two zones 166, 167. As indicated by the arrows, the polymer drug layers 164 in the first zone 166 elute one drug into the vessel lumen 168 for systemic distribution and the polymer drug layers 165 in the second zone 167 elute another drug into the vessel wall 169. The different radial zones allow the suitable drug to be delivered to the suitable place, such as an anti-proliferative or anti-inflammatory drug to the vessel wall, or anti-thrombotic drugs to the luminal environment.

Figure 6:
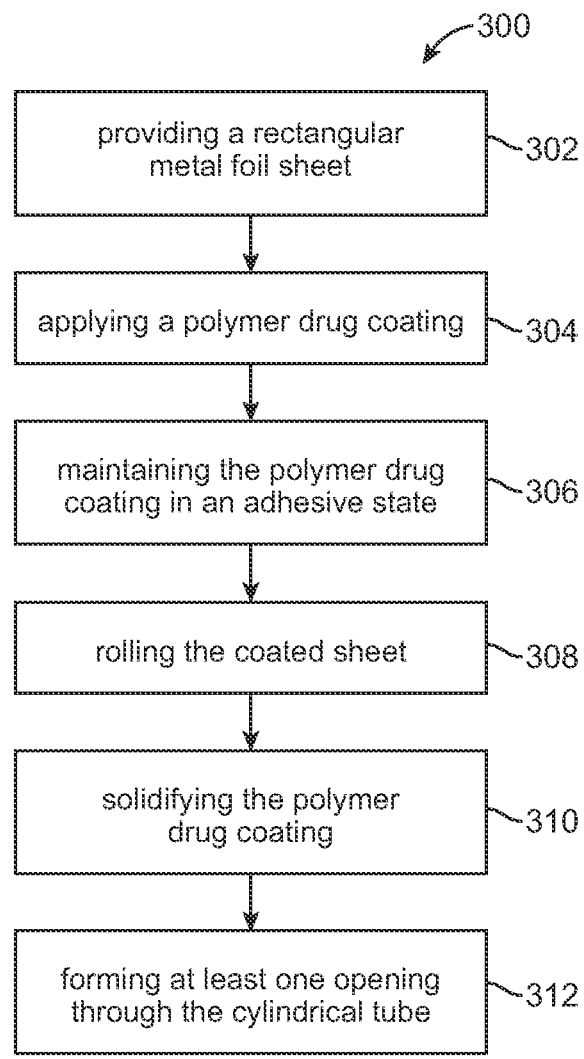
FIG. 6 is a flow chart of a method of manufacture of a drug eluting rolled stent in accordance with the present invention.

FIG. 6 is a flow chart of a method of manufacture of a drug eluting rolled stent in accordance with the present invention. The method 300 includes providing a rectangular metal foil sheet 302 having a first side and a second side; applying a polymer drug coating 304 to the first side of the rectangular metal foil sheet to form a coated sheet; maintaining the polymer drug coating in an adhesive state 306; rolling the coated sheet 308 to form a cylindrical tube having a central axis, the polymer drug coating bridging between the first side and the second side of the coated sheet; solidifying the polymer drug coating 310 to adhere the first side and the second side of the coated sheet; and forming at least one opening through the cylindrical tube 312 perpendicular to the central axis, the at least one opening being shaped to form at least one strut having in cross section polymer drug layers between metal foil layers.

The providing a rectangular metal foil sheet 302 having a first side and a second side can include providing a polished and finished rectangular metal foil sheet, which avoids the need to polish and finish the stent after the struts are formed with the openings.

The applying a polymer drug coating 304 to the first side of the rectangular metal foil sheet to form a coated sheet can include spraying the polymer drug coating on the first side of the rectangular metal foil sheet to form the coated sheet. Those skilled in the art will appreciate that the applying can be performed by spraying, painting, rolling, electrostatic deposition, ink jet coating, spin coating, or the like as desired for a particular application.

The polymer drug coating 304 can be divided into different zones with different polymer-drug combinations. In one embodiment, one zone can include a polymer drug coating with one drug and another zone can include a polymer drug coating with a different drug or no drug. In one embodiment, one zone can include a polymer drug coating with one polymer and another zone can include a polymer drug coating with a different polymer. The combination of zone geometry and polymer drug coating can be selected to provide the desired therapeutic action. In one example, the first zone and the second zone are parallel to the central axis of the cylindrical tube, so that the polymer drug layers vary radially in the finished stent, e.g., the polymer drug layers can be different in different radial polymer drug layers to provide different therapies in the vessel lumen in to the vessel wall. In another example, the first zone and the second zone are perpendicular to the central axis of the cylindrical tube, so that the polymer drug layers vary axially in the finished stent, e.g., the polymer drug layers can be different at the end of the stent to account for edge dissection. In yet another example, the first zone can include a polymer compatible with a first drug and the second zone can include a different polymer compatible with a second drug but incompatible with the first drug. Those skilled in the art will appreciate that a number of zones with different polymer drug coatings can be used as desired for a particular application.

The maintaining the polymer drug coating in an adhesive state 306 keeps the polymer drug coating flexible so that the polymer drug coating can fill the area between the first side and the second side of the coated sheet and stick to both the first side and the second side of the coated sheet. In one embodiment, the polymer drug coating stays in an adhesive state as volatile compounds evaporate. In another embodiment, the maintaining the polymer drug coating in an adhesive state 306 can include heating the polymer drug coating.

The rolling the coated sheet 308 forms a cylindrical tube having a central axis forms the diameter of the stent. The polymer drug coating bridges between the first side and the second side of the coated sheet, conforming to and filling the spiral void between the first side and the second side of the coated sheet. The polymer drug coating also adheres the first side to the second side of the coated sheet. In one embodiment, the coated sheet is rolled around a mandrel. The cross section of the coated sheet in the cylindrical tube forms a continuous spiral perpendicular to the central axis. Until the polymer drug coating solidifies, the coated sheet can be held as the cylindrical tube with an external restraint or the end of the rectangular metal foil sheet can be tacked down.

The solidifying the polymer drug coating 310 adheres and connects the first side and the second side of the coated sheet. The solidifying can include curing, drying, and/or cooling the coated sheet.

The forming at least one opening through the cylindrical tube 312 perpendicular to the central axis cuts the stent into a final geometry, such as a web stent, helical stent, or the like. The opening or openings are shaped to form the strut or struts with polymer drug layers between metal foil layers when viewed in cross section. In one embodiment, the opening or openings are cut with a laser. When the method 300 starts with a polished and finished rectangular metal foil sheet, little polishing and/or finishing of the stent is required. The strut or struts of the stent can then be crimped to a balloon operably attached to a catheter when the stent is a balloon expandable stent.

FIGS. 7A-7G, in which like elements share like reference numbers, are various views of a method of manufacture of a drug eluting rolled stent in accordance with the present invention.

Figure 7A:
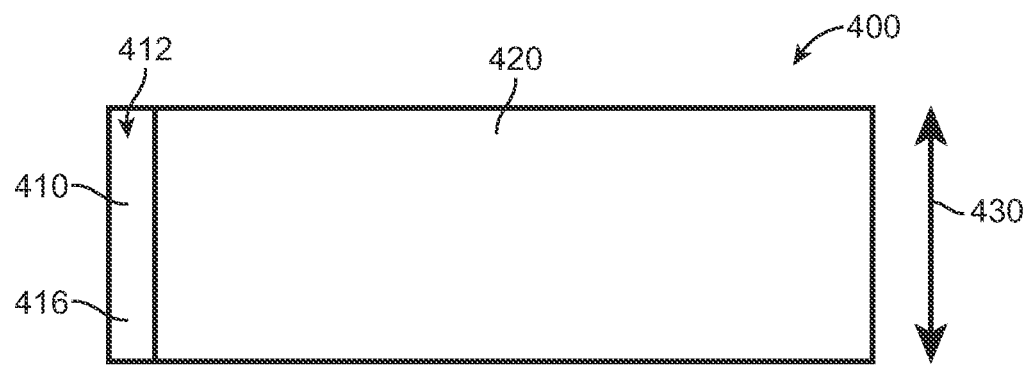
Figure 7B:
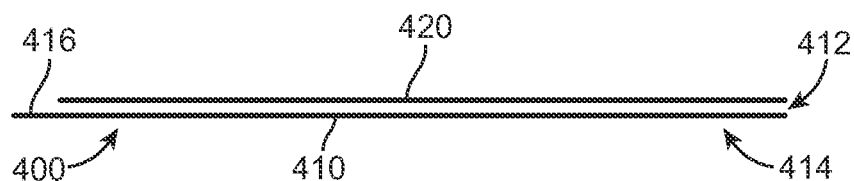

FIGS. 7A and 7B are top and side views, respectively, of a coated sheet for use in a method of manufacture of a drug eluting rolled stent in accordance with the present invention. The coated sheet 400 includes a rectangular metal foil sheet 410 and a polymer drug coating 420. The rectangular metal foil sheet 410 has a first side 412 and a second side 414. The polymer drug coating 420 is applied to the first side 412 to form the coated sheet 400. In this example, the longer dimension of the rectangular metal foil sheet 410 is perpendicular of the central axis 430 about which the cylindrical tube is formed. In this example, the rectangular metal foil sheet 410 has a tack portion 416 which is uncoated. After the coated sheet 400 has been rolled into the cylindrical tube, the tack portion 416 is tacked in place to hold the cylindrical tube in a fixed configuration until the polymer drug coating 420 solidifies.

The materials of the coated sheet 400 can be any biocompatible materials appropriate to the particular application. The rectangular metal foil sheet 410 can be any biocompatible metal, such as stainless steel, cobalt alloy, cobalt chromium alloy, magnesium, or the like. The dimensions of the rectangular metal foil sheet 410 can be selected as desired for a particular application. Those skilled in the art will appreciate that rectangular as defined herein with reference to the rectangular metal foil sheet 410 is not limited to the strict geometrical definition and that the shape of the rectangular metal foil sheet can be any sheet that can be rolled into a generally cylindrical tube. The length of the rectangular metal foil sheet 410 perpendicular to the central axis 430 can be selected to provide the desired number of metal foil layers and polymer drug layers. The thickness of the metal foil forming the rectangular metal foil sheet 410 and the number of metal foil layers can be selected to provide the desired stiffness and mechanical characteristics for the stent. In one example, the thickness of the rectangular metal foil sheet 410 can be between 50 and 100 µm. As used herein in terms such as rectangular metal foil sheet and metal foil layers, the term metal foil is defined as a thin metal which, when formed into a stent by itself, lacks the stiffness and/or strength to support a vessel wall when the stent is in the expanded condition. The metal foil requires a number of metal foil layers adhered and connected by interleaved polymer drug layers to form a stent with sufficient stiffness and/or strength to support a vessel wall. The rectangular metal foil sheet 410 can be polished and finished before application of the polymer drug coating 420 to reduce the finishing work after cutting openings to form the stent.

The polymer drug coating 420 includes a polymer and a drug. Exemplary polymers include any polymer compatible with a selected drug or therapeutic agent, i.e., polymers such as BioLinx® polymer, poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, combinations thereof, and the like.

Those skilled in the art will appreciate that any compatible combinations of polymer and drug can be used as desired for a particular application.

Exemplary drugs include any drug, therapeutic agent, or bioactive agent that can diffuse through a selected polymer, such as an antirestenotic drug (e.g., rapamycin, rapamycin analogue, or rapamycin derivative to prevent or reduce the recurrence or narrowing and blockage of the bodily vessel), an anti-cancer drug (e.g., camptothecin or other topoisomerase inhibitors), an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, a combination thereof, and the like. Those skilled in the art will appreciate that in another embodiment that the drug can be omitted from the polymer drug coating 420, so that the polymer drug coating 420 is polymer alone without a drug.

Figure 7C:
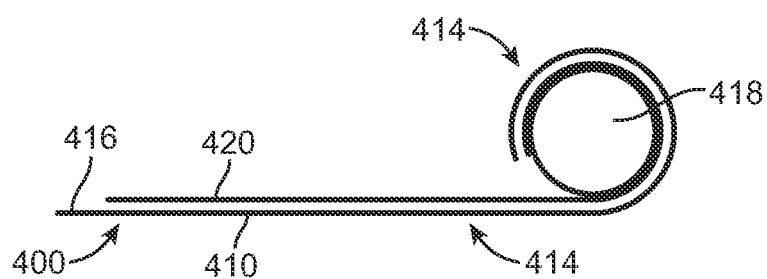

FIG. 7C is a side view of rolling a coated sheet into a cylindrical tube for use in a method of manufacture of a drug eluting rolled stent in accordance with the present invention. In this example, the coated sheet 400 is being rolled about a mandrel 418 having an outer diameter as desired for the stent lumen inner diameter. The mandrel 418 can be removed from the cylindrical tube after the cylindrical tube is formed. In one embodiment, the mandrel 418 is removed before the polymer drug coating solidifies. In another embodiment, the mandrel 418 is removed after the polymer drug coating solidifies.

FIGS. 7D, 7E, and 7F are side, wall cross section, and transverse cross section views, respectively, of a cylindrical tube for use in a method of manufacture of a drug eluting rolled stent in accordance with the present invention. The cylindrical tube 440 is formed by rolling the coated sheet 400. In one embodiment, the coated sheet is rolled around a mandrel of an outer diameter desired for the stent lumen inner diameter. The second side 414 of the coated sheet is located on the outside of the cylindrical tube 440, which has a central axis 430. The wall of the cylindrical tube 440 in cross section includes metal foil layers 442 alternating with polymer drug layers 444, due to the spiral cross section of the cylindrical tube 440 perpendicular to the central axis 430.

FIG. 7G is a side view of a cylindrical tube with openings for use in a method of manufacture of a drug eluting rolled stent in accordance with the present invention. In this example, the cylindrical tube 440 includes a number of openings 450 to form a web stent with the struts in a W-shaped pattern. Those skilled in the art will appreciate that the openings can be formed in any pattern desired to form a stent of a particular design, such as a web stent, helical stent, or the like. In one embodiment, the openings 450 can be formed by cutting with a laser. In other embodiments, the openings 450 can be formed with any cutting device desired for a particular application.

Figure 8A:
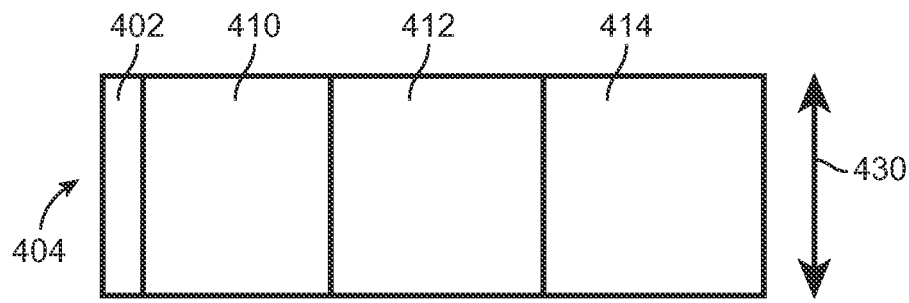
FIGS. 8A-8C are various embodiments of a rectangular metal foil sheet for use in a method of manufacture of a drug eluting rolled stent in accordance with the present invention.
Figure 8B:
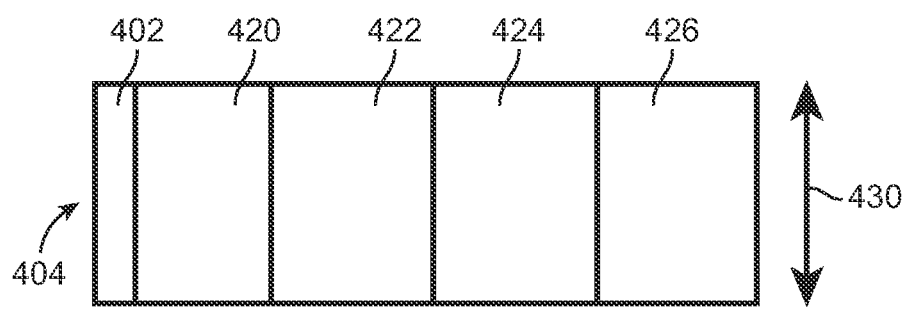
Figure 8C:
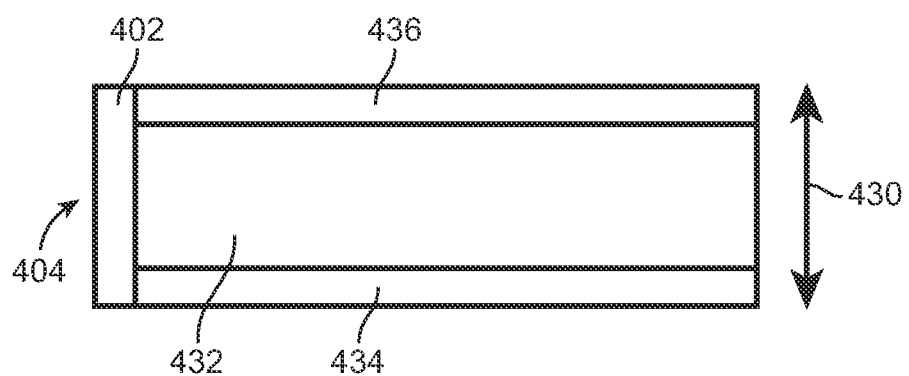

FIGS. 8A-8C, in which like elements share like reference numbers, are top views of a coated sheet for use in a method of manufacture of a drug eluting rolled stent in accordance with the present invention. The coated sheet includes a number of zones of polymer drug coatings which can include different polymer-drug combinations.

Referring to FIG. 8A, the first side 402 of the rectangular metal foil sheet 404 in this example includes three zones 410, 412, 414 of the polymer drug coating in the coated sheet at different distances from the central axis 430. In one embodiment, the three zones 410, 412, 414 each have a different polymer-drug combination, so the rolled stent includes three different radial polymer drug layers. In another example, the outer zones 410, 414 have one polymer-drug combination and the drug is omitted from the middle zone 412, so the middle radial polymer drug layers in the rolled stent include polymer but no drug.

Referring to FIG. 8B, the first side 402 of the rectangular metal foil sheet 404 in this example includes four zones 420, 422, 424, 426 of the polymer drug coating in the coated sheet at different distances from the central axis 430. The four zones 420, 422, 424, 426 can include different polymer-drug combinations, so the rolled stent includes three different radial polymer drug layers. Those skilled in the art will appreciate that the number of zones can be selected to provide the desired number of radial polymer drug layers of a particular polymer-drug combination desired for a particular application.

Referring to FIG. 8C, the first side 402 of the rectangular metal foil sheet 404 in this example includes three zones 436, 432, 434 of the polymer drug coating in the coated sheet perpendicular to the central axis 430. Axial variation in the polymer drug layers of the rolled stent can be used to vary the drug supplied axially for conditions such as edge dissection, i.e., damage to the vessel wall at the ends of the stent. In one embodiment, the three zones 436, 432, 434 can each include different polymer-drug combinations, so the rolled stent includes three different polymer drug layers at different axial locations. In another embodiment, the outer zones 436, 434 include one drug and the drug is omitted from the middle zone 432, so the rolled stent axially includes one drug at the ends and no drug in the middle. In yet another embodiment, the outer zones 436, 434 include one drug and the middle zone 432 includes another different drug, so the rolled stent axially includes one drug at the ends and a different drug in the middle.

It is important to note that FIGS. 1-8 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
   a catheter;
   a balloon operably attached to the catheter; and
   a stent disposed on the balloon;
   wherein the stent comprises:
   a rectangular metal foil sheet having a first side and a second side, the rectangular metal foil sheet being rolled with the first side across from the second side to form a cylindrical tube having a central axis and a spiral cross section perpendicular to the central axis;
   a polymer drug coating disposed between and attached to both-the first side and the second side to adhere and connect the first side to the second side wherever the first side is across from the second side; and
   at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

2. The stent delivery system of claim 1 wherein the polymer drug layers include one drug in a first radial polymer drug layer and a second drug different from the first drug in a second radial polymer drug layer.

3. The stent delivery system of claim 1 wherein at least one of the polymer drug layers comprises polymer alone without drug.

4. The stent delivery system of claim 1 wherein each of the polymer drug layers has a thickness so dimensioned as to provide a predetermined drug elution rate.

5. The stent delivery system of claim 1 wherein the at least one strut has a width so dimensioned as to provide a predetermined drug elution duration.

6. The stent delivery system of claim 1 wherein the at least one opening is a plurality of openings shaped to form a web stent.

7. The stent delivery system of claim 1 wherein the at least one opening is shaped to form a helical stent.

8. A stent comprising:
   a rectangular metal foil sheet having a first side and a second side, the rectangular metal foil sheet being rolled with the first side across from the second side to form a cylindrical tube having a central axis and a spiral cross section perpendicular to the central axis;
   a polymer drug coating disposed between and attached to both-the first side and the second side to adhere and connect the first side to the second side wherever the first side is across from the second side; and
   at least one opening formed through the cylindrical tube generally perpendicular to the central axis, the at least one opening being shaped to form at least one strut having in cross section polymer drug layers between metal foil layers, polymer drug layer edges of the polymer drug layers being in communication with the at least one opening.

9. The stent of claim 8 wherein the polymer drug layers include one drug in a first radial polymer drug layer and a second drug different from the first drug in a second radial polymer drug layer.

10. The stent of claim 8 wherein at least one of the polymer drug layers comprises polymer alone without drug.

11. The stent of claim 8 wherein each of the polymer drug layers has a thickness so dimensioned as to provide a predetermined drug elution rate.

12. The stent of claim 8 wherein the at least one strut has a width so dimensioned as to provide a predetermined drug elution duration.

13. The stent of claim 8 wherein the at least one opening is a plurality of openings shaped to form a web stent.

14. The stent of claim 8 wherein the at least one opening is shaped to form a helical stent.

* * * * *